(12) United States Patent
Chen (10) Patent No.: US 7,902,162 B2
(45) Date of Patent: Mar. 8, 2011

(54) MEDICAMENT AND METHOD FOR TREATING RECURRENT SPONTANEOUS ABORTION

(75) Inventor: Fenglin Chen, Beijing (CN)

(73) Assignee: Beijin Xinjing Antai Medical and Technology Service Limited Corp, Beijing (CN)

(*) Notice: Subject to any disclaimer, the term of this patent is extended or adjusted under 35 U.S.C. 154(b) by 1154 days.

(21) Appl. No.: 10/585,623

(22) PCT Filed: Feb. 20, 2004

(86) PCT No.: PCT/CN2004/000135
§ 371 (c)(1),
(2), (4) Date: Jul. 11, 2006

(87) PCT Pub. No.: WO2005/079814
PCT Pub. Date: Sep. 1, 2005

(65) Prior Publication Data
US 2009/0131345 A1    May 21, 2009

(51) Int. Cl.
*A01K 43/04* (2006.01)
*A61K 31/715* (2006.01)

(52) U.S. Cl. .................................................. 514/44
(58) Field of Classification Search .................... 514/44; 424/93.2, 93.21
See application file for complete search history.

(56) References Cited

U.S. PATENT DOCUMENTS

| 4,444,879 | A | 4/1984 | Foster et al. |
| 5,281,522 | A | 1/1994 | Senyei et al. |
| 5,468,619 | A | 11/1995 | Senyei et al. |

FOREIGN PATENT DOCUMENTS

| CA | 2 358 146 | 9/2001 |
| CA | 2 358 146 | 3/2003 |
| DE | 28 36 362 | 3/1980 |
| JP | 9-218202 | 8/1997 |
| WO | 83/00877 | 3/1983 |
| WO | 02/42769 | 5/2002 |

OTHER PUBLICATIONS

Gatenby (Am. J. Reprod. Immunol., 1993, vol. 29, No. 2, p. 88-94).*
Stricker, R., et al. "Successful treatment of immunologic abortion with low-dose intravenous immunoglobulin." Fertility and Sterility (2000) vol. 73, No. 3, pp. 536-540.
Pandey, M., et al. "Lymphocyte immunotherapy and its probable mechanism in the maintenance of pregnancy in women with recurrent spontaneous abortion." Arch Gynecol Obstet (2004) vol. 269, pp. 161-172.
Ramhorst, R., et al. "Intracellular expression of CD69 in endometrial and peripheral T cells . . . leukocyte immunotherapy." American Journal of Reproductive Immunology (2003) vol. 49, pp. 149-158.
Stricker, R., et al. "Successful treatment of immunologic abortion with low-dose intravenous immunoglobulin." *Fertility and Sterility*, vol. 73, No. 3 (Mar. 2000), pp. 536-540.
Ramhorst, R., et al. "Intracellular Expression of CD69 in Endometrial and Peripheral T cells Represents a Useful Marker in Women with Recurrent Miscarriage: Modulation After Allogeneic Leukocyte Immunotherapy." *American Journal of Reproductive Immunology*, vol. 49, No. 3 (Mar. 2003), pp. 149-158.
Pandey, M.K., et al. "Lymphocyte immunotherapy and its probable mechanism in the maintenance of pregnancy in women with recurrent spontaneous abortion." *Archives of Gynecology and Obstetrics*, vol. 269 No. 3 (Mar. 2004), pp. 161-172.
English Abstract: American Chemical Society. Ogasawara, M. et al. "Clinical Significance of β2 Glycoprotein I Dependent Ancicardiolipin Antibody, Lupus Anticoagulant and Antinuclear Antibodies in Patients with Recurrent Miscarriages" *Reproductive Immunology* (1998) vol. 10, pp. 272-276.
English Abstract: American Chemical Society. Kano, T. et al. "The Incidence of Endometriosis and Adenomyosis in Patients with Habitual Abortion in Relation to Immunological Abnormalities" *Nippon Funin Gakkai Zasshi* (1997) vol. 42, No. 2 , pp. 113-118.
Zhang, S. "Methods for Detecting Antinuclear Antibodies and Clinical Significance thereof" *Journal of Nephrophathy, Dialysis and Kidney Trnasplantation* (1995) vol. 4, Issue 5, pp. 495-497.
U.S. Appl. No. 10/586,285, filed Jul. 2006, Chen.
Ksouri, H, et al. "Recurrent pregnancy loss related to immune disorders." *Ann Med Interne* (Paris) (2003) vol. 154, No. 4, pp. 233-247.
Gatenby, P. A., et al. "Treatment of recurrent spontaneous abortion by immunization with paternal lymphocytes." *Am. J. Reprod. Immunol.* (1993) vol. 29, No. 2, pp. 88-94.
Review Article "Recurrent Pregnancy Losses and the Role of Immunotherapy." *Arch Gynecol Obstet* (2000) vol. 264, pp. 3-12.
Feinberg, R. F., et al. "Is Oncofetal Fibronectin a Trophoblast Glue for Human . . . ?" *American Journal of Pathology* (1991) vol. 138, No. 3.
Chakraborty, C., et al. Reaulation of human trophoblast migration and invasiveness.: *Can J Physiol Pharmacol.* (2002) vol, 80, No. 2, pp. 116-124.
Koenn, M. E., et al. "Fetal Fibronectin." *Clin Lab Sci* (2002) vol. 15, No. 2, pp. 96-98, 115.
Ogasawara, M., et al. "Are antinuclear antibodies predictive of recurrent miscarriage?" *Lancet* (1996) vol. 347, pp. 1183-1184.

(Continued)

*Primary Examiner* — Michael C. Wilson
(74) *Attorney, Agent, or Firm* — Ladas & Parry LLP (57) ABSTRACT

The present invention discloses a pharmaceutical composition for treating a subject with immunological recurrent spontaneous abortion which comprises a therapeutically effective amount of a substance capable of lowering the in vivo level of antinuclear antibody. Particularly, the substance is chromosome No. 2 or fragment thereof containing fibronectin encoding gene derived from the spouse of said subject, or a mixture of chromosome No. 2 or fragment thereof containing fibronectin encoding gene derived from a plurality of males. The present invention also discloses a method for treating immunological recurrent spontaneous abortion.

5 Claims, 2 Drawing Sheets

OTHER PUBLICATIONS

Bernasconi, et al. American Journal of Human Genetics (1996) vol. 59, No. 5 pp. 1114-1118.
Maggio, Immunoenzyme Technique 1 (1980) CRC Press, pp. 186-187.
Aoki, et al. American Journal of Reproductive Immunology (1993) vol. 29, pp. 82-87.
Jones, Acta Endrocrinologica (1975) vol. 78, No. Suppl 94, pp. 376-404 (Abstract Only).
Kwak, et al., Journal of Reproductive Immunology (1995) vol. 28, pp. 175-188.
Gafter, U., et al. "Suppressed cell-mediated immunity and monocyte and natural killer cell activity following allogeneic immunization of women with spontaneous recurrent abortion." *Journal of Clinical Immunology* (1997) Plenum Publishing Co., vol. 17, pp. 415-418.
Perdriger, A., et al. "The genetic basis for systemic lupus erythematosus." *Joint Bone Spine* (2003) vol. 70, pp. 103-108.

* cited by examiner

MEDICAMENT AND METHOD FOR TREATING RECURRENT SPONTANEOUS ABORTION

FIELD OF THE INVENTION

The present invention relates to a medicament and a method for treating recurrent spontaneous abortion.

BACKGROUND OF THE INVENTION

Abortion is the termination of pregnancy before the 28$^{th}$ gestational week characterized by expulsion of the fetus and the attachment thereof from a pregnant woman. Abortion can be classified into early abortion (before the 12$^{th}$ gestational week) and late abortion (after the 12$^{th}$ gestational week) based upon its occurring time. Abortion can also be classified into spontaneous abortion and artificial abortion based upon the underlying causes. Artificial abortion is the termination of pregnancy induced by surgical operation or a medicament. Spontaneous abortion is the termination of pregnancy due to natural causes, such as some kind of diseases, without artificial interference. Spontaneous abortion includes accidental spontaneous abortion and recurrent spontaneous abortion.

Recurrent spontaneous abortion (RSA) refers to the phenomenon of two or more consecutive abortions characterized by the termination of fetal development in the same gestational week. Recurrent spontaneous abortion affects 2-3% of pregnant women. RSA can be classified into early RSA and late RSA based upon its occurring time. RSA can also be classified into primary RSA and secondary RSA based upon whether there is a normal pregnancy history before the abortion. Clinically, RSAs are divided into early primary RSA, late primary RSA, early secondary RSA and late secondary RSA based upon the two kinds of classification set forth above.

RSAs can be resulted from many causes including abnormity of chromosome, endocrine imbalance, anatomical abnormality of reproduction organs, bacterial infection, viral infection, blood group incompatibility between mother and fetus and environmental pollution, etc. About half of RSAs still have no known cause, and are called unexplained RSAs. Along with the deep understanding of reproductive immunology and the development of immunological assays, immunological factors are thought to be the main cause of unexplained RSAs (Ksouri H, Zitouni M, Achour W, Makni S, Ben Hassen A., Recurrent pregnancy loss related to immune disorders, Ann Med Interne (Paris). 2003 September; 154(4): 233-47.). RSAs associated with immunological factors are called immunological RSAs.

Epidemiological surveys demonstrate that most of the early secondary RSAs are immunological RSAs.

There are several representative hypotheses about the immunological mechanism of RSA, for example: (1) production of the blocking antibodies (BA), such as anti-paternal cytotoxic antibodies (APCA), anti-idiotypic antibodies (Ab2) and mixed lymphocyte reaction blocking antibodies (MLR-Bf) which can inhibit the attack to fetus by maternal immunological system, is inhibited due to the increased sharing of human leukocyte antigens (HLA) between the couple; (2) overactivity of helper T cell 1 (Th1)-derived cytokines and of natural killer cells (NK); (3) abnormal increase of antiphosphokipid antibodies (APA). APA is a group of autoimmune antibodies including anticardiolipin (aCL) antibodies and lupus anticoagulants, etc.

Since the immune recognition mechanism between pregnant woman and fetus has not been fully revealed, the immunological pathogenesis of RSA has not yet been accurately understood. No method of treatment with definite curative effect is available heretofore. Currently, one widely used method for treating immunological RSA is lymphocyte immunotherapy. Immunotherapy of RSA has been applied both in China and other countries since Taylor and Faulk infused to a patient of unexplained RSA a suspension of mixed leukocytes derived from her spouse in 1981 (Gatenby P A, Cameron K, Simes R J. Treatment of recurrent spontaneous abortion by immunization with paternal lymphocytes: results of a controlled trial. Am J Reprod Immunol. 1993 March; 29(2): 88-94.). The immunogen is lymphocytes from the spouse in most cases. The immunotherapy includes isolating lymphocytes from the spouse's venous blood for intracutaneous injection. Alternatively, the condensed leucocytes or whole blood from the spouse can also be intravenously injected. If the live cells are inactivated by 200 rad X-ray radiation prior to intracutaneous injection, the graft-versus-host reaction can be attenuated. Usually, the immunization is performed every 2 weeks for a total of 2 to 4 times before pregnancy and boosted 1 to 3 times after pregnancy. Twenty years after the application of lymphocyte immunotherapy for treating RSA, a great deal of studies from China and other countries have indicated that the therapeutic effect of this therapy is not definite and the therapy has some serious adverse side effects. Most literatures on immunotherapy of RSA from 1981 to 1994.9 had been reviewed. It was found that only one of the six studies that were worthy of analysis demonstrated the effectiveness of the immunotherapy. There was no statistically significant difference between the therapy group and the control group in the other studies (Yan Jianhua and Zhu Xihua, Discussion about the Scientificalness and Research Strategy of Immunotherapy of Recurrent Spontaneous Abortion, KeXue, 1994.6: 59-62). Charles A. Omwandho et al. (Recurrent Pregnancy Losses and the Role of Immunotherapy. Review Article, Arch Gynecol Obstet (2000) 264:3-12) found that though some experimental data seemed to support the effectiveness of lymphocyte immunotherapy, there was no statistical difference between the clinical cure rates of the therapy group and the control group treated only by a non-immunological method such as psychological support and care etc. The immunotherapies using inactivated bacterium or autologous blood irradiated by ultra violet (UV) after in vitro hemolysis obtained as high cure rate as the lymphocyte immunotherapy. These experimental results questioned the effectiveness of the lymphocyte immunotherapy.

In addition, the lymphocyte immunotherapy has some serious adverse side effects such as erythrocyte sensitization, thrombocytopenia and intrauterine growth retardation of fetus etc. Some diseases transmitted by blood such as AIDS may be transferred from one individual to another due to the living cells with intact nuclear materials are used in lymphocyte therapy.

Thus, there is an urgent need for a method for treating immunological RSA with definite therapeutical effect and less side effects.

The inventor of the present invention provides an efficient and safe immunotherapy of RSA based upon the deep research on the pathogenesis of immunological early secondary RSA.

SUMMARY OF THE INVENTION

The present invention provides:
1. A pharmaceutical composition for treating a subject with recurrent spontaneous abortion characterized by comprising a therapeutically effective amount of chromosome No. 2 or fragment thereof containing fibronectin encoding gene derived from the spouse of said subject.

2. A pharmaceutical composition for treating a subject with recurrent spontaneous abortion characterized by comprising a therapeutically effective amount of a mixture composed of chromosome No. 2 or fragment thereof containing fibronectin encoding gene derived from a plurality of males.

3. Chromosome No. 2 or fragment thereof containing fibronectin encoding gene derived from a male as a medicament.

4. Use of a substance capable of lowering the level of antinuclear antibodies in vivo, particularly chromosome No. 2 or fragment thereof containing fibronectin encoding gene derived from a male, for the preparation of a medicament for treating recurrent spontaneous abortion.

5. A method for treating a subject with recurrent spontaneous abortion comprising administering to the subject in need of treatment a therapeutically effective amount of a substance capable of lowering the level of antinuclear antibodies in vivo.

6. The method according to 5, wherein said substance capable of lowering the level of antinuclear antibodies in vivo is chromosome No. 2 or fragment thereof containing fibronectin encoding gene derived from the spouse of said subject.

7. The method according to 5, wherein said substance capable of lowering the level of antinuclear antibodies in vivo is a mixture of chromosome No. 2 or fragment thereof containing fibronectin encoding gene derived from a plurality of males.

The pharmaceutical compositions and methods for treating RSA provided by the present invention have definite therapeutical effects (cure rate >95%), and no obvious side effects have been detected according to the clinical verification.

DETAILED DESCRIPTION OF THE INVENTION

The inventor of the present invention has carried out a clinical epidemiological study on early secondary RSA. It has been found that among various factors concerned, artificial abortion has the highest correlation with early secondary RSA, most of which happened on the same or almost the same gestational week when the previous artificial abortion was made. There is statistically significant difference between the group of early secondary RSA and the control group (see table 1). Therefore, the inventor of the present invention deduced that artificial abortion was the inducing cause of early secondary RSA.

TABLE 1

Epidemiological investigation on early secondary RSA

| Item | Number of cases (N) | Artificial abortion Number of cases (N) | Percentage (%) | Consistency of timing Number of cases (N) | Percentage (%) |
|---|---|---|---|---|---|
| RSA | 35 | 32 | 91 | 30 | 86 |
| Control | 140 | 28 | 20 | — | — |
| $x^2$ | | 52.4 | | | |
| P | | <0.01 | | | |

In order to explore the pathogenesis of early secondary RSA, the inventor of the present invention had monitored the repregnancy of early secondary RSA patients having a history of artificial abortion. When the cessation of fetal development was observed, conceptus samples with intact placental villi were obtained through drug abortion from RSA patients. The conceptus samples from subjects without RSA were used as control. The collected conceptus samples were observed under microscope and scanning electron microscope and studied by immunohistochemistry assay. It was found that there was no difference between the structures of the placental villi of the two groups under microscope. But under scanning electron microscope, it was found that there was a layer of dense protein net outside the trophocytes of control samples (see FIG. 1) while the trophocytes of RSA samples were naked (see FIGS. 1 and 2). Results of the immunohistochemistry assay demonstrated that there was a fibronectin band between the trophocytes and deciduas and among the trophocytes per se of the control samples, while there was no fibronectin outside the trophocytes of the RSA's samples. Accordingly, the inventor of the present invention hypothesized that the fibronectin band outside trophocytes was the main component of placental immunological barrier, and that impairment of the immunological barrier resulted from the loss of the fibronectin band was the cause of immunological RSA.

In order to find the reason of the loss of the fibronectin band outside the trophocytes of immunological RSA patients, the inventor of the present invention measured the level of anti-FN antibody in serum of 30 subjects suffered from early secondary RSA with a history of artificial abortion by using an anti-FN antibody detection kit. There was no statistical difference between the experimental group and the control group. Surprisingly, the inventor found that the level of anti-nuclear antibody against chromosome No. 2 (containing FN encoding gene) in the sera of the patients (detected according to the method described in Example 2) was significantly higher than that of the control group (see table 2).

Accordingly, the inventor put forward a hypothesis about the pathogenesis of immunological RSA: during the artificial interference in pregnancy such as artificial abortion, the fetal cells are broken and the expressing FN encoding gene originated from the spouse is presented to the maternal immune system as antigen, inducing the appearance of antinuclear antibody against FN encoding gene. When the woman is pregnant again with the same spouse, the antinuclear antibody against FN encoding gene enters into the trophocytes and binds to the expressing FN encoding gene. The FN encoding gene is blocked, therefore the fibronectin band outside the trophocytes can not be formed normally and the integrity of the fetal immunological barrier is impaired. The rejection of the repregnant woman to the fetus results in cessation of fetal development and eventually the abortion.

Fibronctin is a macromolecular multifunctional glycoprotein found in connective tissue, on cell surfaces, in cytoplasm and other body fluids. FN band had been found outside fetal trophocytes. But the FN band was thought only to act in connection between placenta and deciduas (Ronald F. Feinberg, Harvey J. Kliman, and Charles J. Lockwood, Is Oncofetal Fibronectin a Trophoblast Glue for Human Implantation? American Journal of Pathology, Vol. 138, No. 3, March 1991), migration and invasion of trophocytes in decidua (Chakraborty C, Gleeson L M, McKinnon T, Lala P K., Regulation of human trophoblast migration and invasiveness. Can J Physiol Pharmacol. 2002 February; 80(2): 116-24. Review.). It was also suggested that the FN level in cervical secrete was indicative of premature labor (Koenn M E., Fetal fibronectin, Clin Lab Sci. 2002 Spring; 15(2):96-8, 115). The action of FN in the fetal immunological barrier has not been recognized in the prior art. Human FN encoding gene was located at chromosome 2q34 by autoradiography in 1995.

The inventor of the present invention made further research based upon the above studies about the pathogenesis of immunological RSA in attempt to find an effective method for treating immunological RSA. It is surprisingly found that injection, to a subject suffered from immunological early secondary RSA before pregnancy, of chromosome No. 2 containing FN encoding gene derived from her spouse can effectively lower the level of antinuclear antibody against chromosome No. 2 in peripheral blood of the subject (see table 2). Even surprisingly, subjects suffered from immunological RSA can be prevented from abortion by significantly lowering the level of said antinuclear antibody before or during pregnancy.

TABLE 2

Change of the level of antinuclear antibody in serum of RSA patients before and after treatment

| | Number of cases | Mean value of the titer of antinuclear antibody in peripheral blood | Difference between groups |
|---|---|---|---|
| Before chromosome treatment | 35 | 1:254.7 | — |
| After chromosome treatment | 35 | 1:34.6 | — |
| Control group | 45 | 1:38.9 | $P < 0.01$ |

Accordingly, the present invention has demonstrated that immunological recurrent spontaneous abortion correlates directly to the in vivo level of antinuclear antibody of the patients. The immunological recurrent abortion can be treated through lowering the in vivo level of antinuclear antibody.

Accordingly, the present invention provides a method for treating recurrent spontaneous abortion comprising administering to a subject in need of the treatment a therapeutically effective amount of a substance capable of lowering the in vivo level of antinuclear antibody. Said substance capable of lowering the in vivo level of antinuclear antibody can be, for example, chromosome No. 2 or fragment thereof containing fibronectin encoding gene derived from the spouse of the subject to be treated, or a mixture of chromosome No. 2 or fragment thereof containing fibronectin encoding gene derived from a plurality of males. According to the method of the present invention, the level of antinuclear antibody of a subject with immunological RSA can be lowered down and kept on a level safe for gestation for a period of time. If the subject gets pregnant and passes the early stage of pregnancy at the safe level, normal gestation can be carried out.

Accordingly, the present invention relates to the use of a substance capable of lowering the in vivo level of antinuclear antibody for the preparation of a medicament for treating recurrent spontaneous abortion. Particularly, said substance capable of lowering the in vivo level of antinuclear antibody is chromosome No. 2 or fragment thereof containing fibronectin encoding gene derived from a male. Said chromosome No. 2 or fragment thereof may be derived from the spouse of the subject to be treated or is a mixture of chromosome No. 2 or fragment thereof from a plurality of males.

The present invention also provides a pharmaceutical composition for treating recurrent spontaneous abortion characterized by comprising a therapeutically effective amount of chromosome No. 2 or fragment thereof containing fibronectin encoding gene derived from the spouse of said subject or a mixture of chromosome No. 2 or fragment thereof containing fibronectin encoding gene from a plurality of males.

As demonstrated in a preliminary clinical trial, the pharmaceutical composition and method of the present invention can treat immunological RSA effectively.

In a preferred embodiment of the present invention, isolated and intact chromosome No. 2 is used.

In another preferred embodiment of the present invention, isolated chromosome No. 2 from cells in M phase is used.

Without being restricted to any theory, the inventor hypotheses that, in patients with immunological RSA, the FN band outside the placental trophocytes can't be normally formed due to the increased level of antinuclear antibody against FN encoding gene. Therefore, injection of a substance capable of lowering the in vivo level of antinuclear antibody (such as spouse-derived chromosome No. 2 containing FN encoding gene) to the patient concerned can neutralize the corresponding antinuclear antibody and lower its level to the extent that it is insufficient to block the expressing FN encoding gene. Then, the fetal FN encoding gene can be expressed normally to form FN band outside the trophocytes during gestation. Therefore, the fetal immunological barrier is well formed to protect the fetus to pass through the gestational week when abortion used to happen, and to develop normally to mature.

In an embodiment of a pharmaceutical composition of the present invention, a therapeutically effective amount of a mixture of chromosome No. 2 or fragment thereof derived from a plurality of males is used. In the embodiment of the present invention, the number of said plurality of males is, for example, at least about 3. Preferably the number is about 5, more preferably about 10, 15, 20, 25, 30 or more. The present invention also relates to a mixture of chromosome No. 2 or fragment thereof derived from a plurality of males as a medicament, use of said mixture in the preparation of a medicament for treating RSA and a method for treating RSA by administering to a patient an effective amount of the mixture.

As used herein, the following terms have the meanings as follows:

Subject (patient): any female mammal including human.

Spouse: the sexual partner of the RSA subject responsible for the aborted gestations.

Chromosome No. 2: human chromosome No. 2 or the corresponding chromosome of other mammals containing FN encoding gene. For other mammals, as long as it contains FN encoding gene, the serial number of said chromosome is not necessarily No. 2 in the genome.

Antinuclear antibody: antibodies against various nuclear components, particularly the antibody/antibodies detected according to a method similar to that described in Example 2.

Immunological RSA: early secondary recurrent spontaneous abortion wherein the titer of the antinuclear antibody in serum is higher than 1:64.

Titer (level) of the antibody: the largest diluting factor of sample serum at which the detection of the antibody is still positive by ELISA.

Safe level for pregnancy: the RSA patient's level of antinuclear antibody which is lowered at least by about 30%, preferably at least about 40%, more preferably at least about 50%, 60%, 70% or more, as compared with the original level of the antibody before therapy, or the antibody titer is smaller than about 1:64.

Isolated: chromosome No. 2 is isolated from other cell components (including proteins, other chromosomes, etc.). Preferably, the content of other cell components is less than 10 wt %, more preferably less than 5 wt %, 4 wt %, 3 wt %, 2 wt %, or even less than 1 wt % based upon weight of dry material. Preferably, the content of other chromosomes is less than 10%, more preferably less than 1%.

M phase (mitosis phase): the period from the beginning of to the end of cell mitosis.

Fragment of chromosome: a fragment of chromosome No. 2 that contains FN encoding gene and keeps the activity for decreasing the level of antinuclear antibody of the present invention.

A mixture of chromosomes containing chromosome No. 2 or fragment thereof can be used in the pharmaceutical compositions or methods of the present invention. For example, the mixture is one of all chromosomes isolated from other cell components. As mentioned above, isolated chromosome No. 2 or fragment thereof is preferably used in the present invention.

Chromosome No. 2 of the pharmaceutical composition of the present invention can be derived from any somatocytes, preferably from peripheral blood lymphocytes (PBLs). PBLs can be isolated from peripheral blood through methods well known to the artisan. Preferably, the cells such as PBLs from which chromosome is to be isolated are cultured in vitro for a period of time. For example, lymphocytes are cultured in an ordinary culture medium such as RPMI-1640 or DMEM with fetal calf serum in $CO_2$ incubator (37±0.5° C., 5% $CO_2$) for a suitable period of time, e.g., about 3 to 5 days in general. During the culture, a suitable amount of reagent capable of inhibiting the formation of microbutule such as colchicine, colchicinamide or catharanthine can be added into the culture medium to stop the cell cycle in M phase by inhibiting cell mitosis. Colchicine is preferable. Total chromosomes can be isolated by chemical or physical methods well known to a person skilled in the art such as freezing and thawing cells, alkaline cell-lysing solution or hyposmosis to lyse the cells. Hyposmosis is preferred. Intact chromosome No. 2 can be further isolated by methods well known to a person skilled in the art such as density gradient centrifugation. Alternatively, fragments of the chromosome containing FN encoding gene can be cleaved by enzyme digestion and then isolated and purified. Preferably, the chromosome or fragment of chromosome is used to prepare the formulation immediately after it is purified. Alternatively, it can be made into lyophilized powder by methods well known to a person skilled in the art and stored at a lower temperature, e.g., −70° C. for future use.

The pharmaceutical composition of the present invention is usually formulated into injection solution. Carrier such as sterile water for injection or physiological saline can be mixed with a suitable amount of chromosome No. 2 or fragment thereof containing FN encoding gene by a conventional method to formulate the injection solution. There is no particular restriction to the concentration of chromosome No. 2 or fragment thereof in the preparation as long as the final preparation is suitable for subcutaneous injection. For example, the concentration is about 2-15, preferably 5-10, more preferably 10 chromosomes per field of oil immersion objective. While being used to treat immunological RSA, the pharmaceutical composition of the present invention is generally injected subcutaneously, preferably in the upper arm. The dosage and times of injection during each course of treatment can be decided by physicians in order to lower the level of antinuclear antibody in the patient's peripheral blood to the extent that is safe for pregnancy. For example, 0.5-2.0 ml injection solution containing chromosome No. 2 or fragment thereof at a concentration as mentioned above is injected each time. Generally, the injection is performed 3 to 5 times, preferably 4 times during 30 days for each course of treatment. When one course of treatment is finished, the level of antinuclear antibody in peripheral blood is determined. If the level of the antibody is lowered down to the extent that is safe for gestation, the patient is ready for pregnancy. For example, after one course of treatment, the level of antinuclear antibody safe for gestation can be maintained for about 3 months during which the patient can safely become pregnant. Preferably, another course of treatment is performed after pregnancy to consolidate the therapeutic effect.

The pharmaceutical composition and method of the present invention have been used in a preliminary clinical trial in which more than 300 patients were included. The cure rate is more than 95% and no side effect has been found. As a new method for treating immunological RSA, gene immunotherapy of the present invention is compared with the existing lymphocyte immunotherapy (Table 3).

TABLE 3

Comparison between the immunotherapy of the present invention and the lymphocyte immunotherapy

|  | Immunotherapy of the present invention | Lymphocytes Immunotherapy |
|---|---|---|
| Method | Injecing the chromosome vaccine subcutaneously to desensitize | Transfusing lymphocytes |
| Therapeutic effect | Definite, >95% | No significant therapeutic effect |
| Side effects | No significant side effect has been found | Transfusion reactions Autoimmune diseases Supersensitivity to erythrocyte and platelet Infections Intra-uterine growth retardation Graft versus host disease Thrombocytopenia Neonatal death |
| Risk of blood infection | Extremely low | High |
| Incidence of side effects | Extremely low | High |

The present invention is further illustrated by the drawings and specific examples which are not intended to limit the scope of the present invention.

EMBODIMENTS OF THE INVENTION

Example 1

Loss of the Fibrotin Band Outside the Fetal Trophocytes in Early Secondary RSA Cases (1) A number of early secondary RSA patients with a history of artificial abortion were monitored when they got pregnant again. When the termination of fetal development was detected, fetus samples of RSA with intact placental villus were obtained by drug abortion.

(2) Fetus samples from subjects without a history of RSA were obtained by drug abortion and used as control.

(3) Placenta samples were fixed by 10% neutral formalin, dehydrated, embedded in paraffin, sliced to 4-5 μm tissue slices, and stained with HE. It was observed that there was no significant difference between the two groups of placental tissue under microscope.

Figure 1:
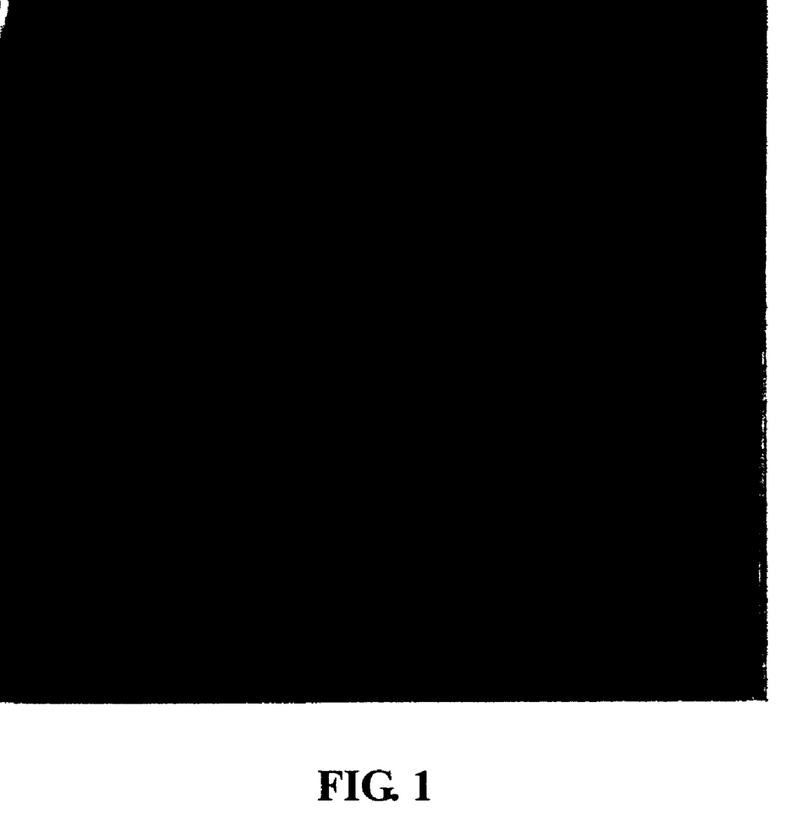
FIG. 1 is a photo of normal placenta of control sample under scanning electron microscope. It can be observed that there is a layer of dense protein net outside the trophocytes.
Figure 2:
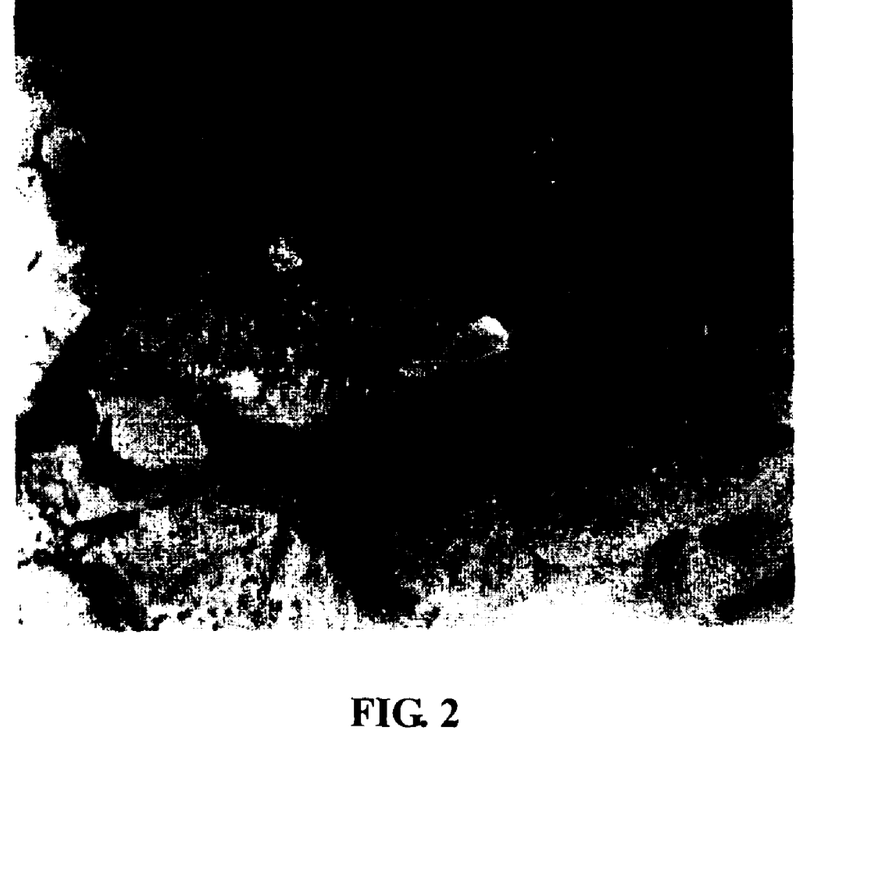
FIG. 2 is a photo of RSA patient's placenta sample under scanning electron microscope. It can be observed that the trophocytes are naked.

(4) Fresh placenta samples were fixed by 2.5% glutaraldehyde and made into slices by a conventional method to observe under transmission electron microscope. It was found that there was a dense protein net outside the trophocytes of control samples, while the trophocytes of the RSA patients' samples were naked. The results are shown in FIGS. 1 and 2.

(5) Expression of fibronectin in the two groups of placental samples was detected by conventional immunohistochemistry using mouse anti-human FN monoclonal antibody (purchased from DAKO, 1:50 diluted) and DAB as substrate. The results demonstrated that there was fibronectin band between the trophoblast and caduca, and also among the trophocytes in the control samples, while there was no fibronectin band outside the trophocytes of RSA patient's samples.

Example 2

Determination of the Level of Antinuclear Antibody in Peripheral Blood of Early Secondary RSA Patients (1) Mixture of chromosome No. 2 derived from a plurality of men (generally more than 20) was prepared.

(2) The mixture of chromosome No. 2 was diluted to the concentration of 10 chromosomes per field of oil immersion objective by coating buffer (0.05M sodium carbonate buffer, pH 9.6) to coat polystryrene microplate (ELISA plate).

(3) 50 μl of a patient's serum diluted by different diluting factors (1:64, 1:128, 1:256, 1:512, 1:1024) by buffer (PBS buffer containing 0.1% bovine serum albumin, pH 7.4) was added to each reaction well. The reaction lasted for 30 minutes at 37° C. Then the reaction wells were rinsed by PBS buffer (pH 7.4) twice.

(4) 50 μl of mouse anti-human IgG antibody labeled with horse radish peroxidase (purchased from DAKO) was added into each reaction well. The reaction lasted for 30 minutes at 37° C. Then the reaction wells were rinsed by PBS buffer (pH 7.4) twice.

(5) 0.1 ml solution of substrate TMB (3,3',5,5'-Tetramethylbenzidine) which was freshly prepared by a conventional method was added into each reaction well. The reaction lasted for 10 to 30 minutes at 37° C.

(6) The OD value of each reaction well was read by microplate reader to determine the level of antinuclear antibody. Alternatively, the maximal diluting factor of serum at which the color reaction can still be observed by naked eye is deemed as the titer of antinuclear antibody.

If the color reaction can still be observed at a diluting factor of serum more than 1:64, it is clinically significant.

Example 3

Preparation of the Pharmaceutical Composition of the Present Invention (1) 80 ml venous blood was taken from the spouse of the patient. An appropriate amount of heparin (5000 IU) was added as anticoagulant.

(2) The 80 ml venous blood was allocated into 16 tubes, 5 ml each. 5 ml Ficoll lymphocyte separation medium (purchased from Sino-American Company) was added into each tube. The tubes were centrifuged at 2000 rpm for 10 minutes and the supernatant was discarded. 10 ml of PBS buffer (pH 7.6) was added to each tube to resuspend the lymphocytes. The lymphocyte suspension was centrifuged at 5000 rpm for 10 minutes. The supernatant was discarded. This process was repeated once more. 10 ml culture medium of RPMI-1640 was added to the lymphocyte pellet of each tube to resuspend the lymphocytes. The resuspended lymphocytes were transferred into cell culture flasks. Then, 10 ml culture medium was added into each culture flask.

(3) The lymphocytes were cultured in a $CO_2$-incubator (37° C.±0.5° C., 5% $CO_2$) for 4 days. 0.05 ml to 0.1 ml 40 μg/ml solution of colchicine was added into each culture flask on the third day. The lymphocytes were cultured for another day. On the fourth day, the cells attached to the culture flask were blown off and centrifuged at 5000 rpm for 10 minutes. The supernatant was discarded and the cell pellets were kept.

(4) 5 ml of 0.06 wt % KCl solution was added into the lymphocyte pellets to suspend and lyse the cells. The suspension was kept at room temperature for 30 minutes and centrifuged at 10000 rpm for 10 minutes. The supernatant was discarded.

(5) The lymphocyte lysate was rinsed twice with 5 ml PBS buffer (pH7.6).

(6) The lymphocyte lysate was resuspended with 5 ml PBS buffer (pH7.6). After 10 ml separation medium of 50% saccharose was added, the suspension was centrifuged at 5000 rpm for 10 minutes. The supernatant was kept.

(7) After 10 ml separation medium of 40% saccharose was added, the supernatant was centrifuged at 5000 rpm for 10 minutes. The pellet was kept.

(8) The pellet was rinsed twice with 2 ml PBS buffer (pH7.6).

(9) The pellets derived from 20 ml peripheral blood were resuspended in 1 ml physiological saline and stored at −20° C. The suspension made from the spouse's 20 ml peripheral blood was injected subcutaneously to the patient in upper arm for each time of immunotherapy injection.

Note: All the operations and reagents should be kept sterile.

Example 4

Case 1

The patient had been married for 5 years when she visited the doctor for RSA. Her first and second gestations during 1993-1995 were ended by artificial abortion on the $7^{th}$ gestational week. She wanted a baby when she was pregnant in 1996 for the third time. However, on the $8^{th}$ gestational week, the patient had abdominal pain and then bled from vagina. Ultrasonic detection showed the termination of the fetal development. Then the abortion happened. The patient got pregnant twice during 1997-1998. Hematic secretion appeared in vagina on the $7^{th}$ gestational week of each gestation. Traditional Chinese medicament containing gesterol had been used to protect the fetus from abortion and bleeding stopped. On the $10^{th}$ gestational week, ultrasonic detection showed the termination of the fetal development. Drug abortion was performed. The dead fetus was about 7 gestational weeks old. Artificial contraception had been carried out since January 1998. The level of antinuclear antibody in peripheral blood of the patient before therapy was determined to be 1:128 according to the method in Example 2.

The pharmaceutical composition of the present invention made from the chromosome of the patient's husband according to Example 3 was subcutaneously injected to the patient for four times on Sep. 6, Sep. 12, Sep. 25 and Oct. 19, 1998 respectively. For the first three times, the topical reaction strength on the skin after injection was ++++. For the fourth time, the reaction strength was ++. The patient's level of antinuclear antibody in peripheral blood was lowered to 1:64 after the fourth injection.

The patient born a healthy boy baby weighed 2800 g in September 1999.

Example 5

Case 2

The patient had been married for 4 years when she visited the doctor for RSA. Her first gestation in 1995 was ended by artificial abortion on the $7^{th}$ gestational week. She wanted a baby when she was pregnant in August 1996 for the second time. On the $7^{th}$ gestational week, the patient had abdominal pain and then bled from vagina. Ultrasonic detection showed the termination of the fetal development. Then, complete abortion happened. The patient got pregnant twice during 1997.1-1997.6. Hematic secretion appeared in vagina on the $8^{th}$ and $7^{th}$ gestational week respectively. Traditional Chinese medicament containing gesterol had been used to protect the fetus from abortion and bleeding stopped. On the $10^{th}$ gestational week, ultrasonic detection showed the termination of the fetal development. Drug abortion was performed. The dead fetus was about 8 gestational weeks old. Artificial contraception had been carried out since 1997.7. The level of antinuclear antibody in peripheral blood of the patient before therapy was determined to be 1:1024 according to the method in Example 2.

The pharmaceutical composition of the present invention made from the chromosome of the patient's husband according to Example 3 was subcutaneously injected to the patient for four times on Jun. 25, Jul. 12, Jul. 28 and Aug. 12, 1999, respectively. For the first three times, the topical reaction strength on the skin after injection was ++++. For the fourth time, the reaction strength was ++. The patient's level of antinuclear antibody in peripheral blood was lowered to 1:64 after the fourth injection.

The patient born a healthy boy baby weighed 3000 g in May 2000.

Example 6

The medicament and method of the present invention have been used in preliminary clinical trials in a few Chinese hospitals. More than patients which were recruited according to the criteria of early secondary RSA, a history of artificial abortion, increased level of specific antinuclear antibody in peripheral blood (>1:64) have been treated. The cure rate is more than 95%. Except the normal therapeutic reactions such as local congestion, swelling, fever and pain etc. at the inoculating site, no side effect has been observed. The therapeutic effect of the method of the present invention and that of the lymphocyte immunotherapy reported by literatures are compared as follows.

TABLE 4

Comparison of therapeutic effects between the immunotherapy of the present invention and lymphocyte immunotherapy

| Immunogen | Immunotherapy of the present invention Chromosome No. 2 derived from the spouse | Lymphocyte immunotherapy[1] Suspension of lymphocytes derived from the spouse | P value |
| --- | --- | --- | --- |
| Number of cases | 300 | 21 | |
| Number of successful gestations | 287 | 13 | |
| Cure rate | >95% | 62% | <0.01 |

[1]Cauchi M N et al., Am. J. Reprod. Immunol. 1991; 25: 16.

The invention claimed is:

1. A method of treating a human subject with immunological, recurrent, spontaneous abortion comprising administering to said subject a therapeutically effective amount of chromosome No. 2 obtained from a human male, wherein said chromosome 2 is isolated from somatocytes in M phase.

2. A method of treating a human subject with immunological, recurrent, spontaneous abortion comprising administering to said subject a therapeutically effective amount of chromosome No. 2 obtained from a plurality of human males, wherein said chromosome No. 2 is isolated from somatocytes in M phase.

3. The method according to claim 2, wherein the number of said plurality of males is more than 3.

4. The method according to claim 3, wherein the number of said plurality of males is more than 10.

5. The method according to claim 4, wherein the number of said plurality of males is more than 20.

* * * * *

UNITED STATES PATENT AND TRADEMARK OFFICE
CERTIFICATE OF CORRECTION

| | | |
|---|---|---|
| PATENT NO. | : 7,902,162 B2 | Page 1 of 1 |
| APPLICATION NO. | : 10/585623 | |
| DATED | : March 8, 2011 | |
| INVENTOR(S) | : Fenglin Chen | |

It is certified that error appears in the above-identified patent and that said Letters Patent is hereby corrected as shown below:

Title page, item (73), assignee: "Beijin" should read --Beijing--.

Signed and Sealed this
Twenty-sixth Day of July, 2011

David J. Kappos
*Director of the United States Patent and Trademark Office*